US011439159B2

(12) United States Patent
Hume et al.

(10) Patent No.: US 11,439,159 B2
(45) Date of Patent: Sep. 13, 2022

(54) SYSTEM FOR IDENTIFYING AND DEVELOPING INDIVIDUAL NATURALLY-OCCURRING PROTEINS AS FOOD INGREDIENTS BY MACHINE LEARNING AND DATABASE MINING COMBINED WITH EMPIRICAL TESTING FOR A TARGET FOOD FUNCTION

(71) Applicant: Shiru, Inc., Alameda, CA (US)

(72) Inventors: Jasmin Hume, Orinda, CA (US); Geoffroy Dubourg-Felonneau, Berkeley, CA (US); Akemi Kunibe, San Francisco, CA (US); Lawrence Lee, San Francisco, CA (US)

(73) Assignee: Shiru, Inc., Alameda, CA (US)

( * ) Notice: Subject to any disclaimer, the term of this patent is extended or adjusted under 35 U.S.C. 154(b) by 0 days.

(21) Appl. No.: 17/520,201

(22) Filed: Nov. 5, 2021

(65) Prior Publication Data

US 2022/0104515 A1      Apr. 7, 2022

Related U.S. Application Data

(60) Provisional application No. 63/163,949, filed on Mar. 22, 2021.

(51) Int. Cl.
*A23J 3/00* (2006.01)
*A23J 3/04* (2006.01)
(Continued)

(52) U.S. Cl.
CPC .............. *A23J 3/04* (2013.01); *G06K 9/6256* (2013.01); *G06N 20/00* (2019.01); *G16H 20/60* (2018.01)

(58) Field of Classification Search
None
See application file for complete search history.

(56) References Cited

U.S. PATENT DOCUMENTS 10,962,473 B1 * 3/2021 O'Hara ................ G06N 5/04
2003/0097227 A1 * 5/2003 Bloch .................. G16B 40/00
702/75

(Continued)

FOREIGN PATENT DOCUMENTS

WO    WO-2021050923 A1 * 3/2021

OTHER PUBLICATIONS

Learned protein embeddings for machine learning. Yang KK, Wu Z, Bedbrook CN, Arnold FH. Bioinformatics. Aug. 1, 2018;34(15):2642-2648.

(Continued)

*Primary Examiner* — John A Pauls
(74) *Attorney, Agent, or Firm* — MS IP Law

(57) ABSTRACT

This disclosure provides a technology for developing alternative protein sources for use in industrial food production. The technology mines natural sources by a process that is done partly in silico. Instead of sampling and testing a vast library of compounds, machine learning and implementation narrows the field of functional candidates by predictive modeling based on known protein structure. Candidate proteins that are selected by this analysis are then produced and screened in a high-throughput manner by recombinant expression and testing to determine whether they have a target function. Multiple cycles of the machine learning, database mining, expression and testing are done to yield potential ingredients suitable for assessment as part of a commercial food product.

24 Claims, 8 Drawing Sheets

(51) Int. Cl.
  *G06K 9/62* (2022.01)
  *G06N 20/00* (2019.01)
  *G16H 20/60* (2018.01)

(56) References Cited

U.S. PATENT DOCUMENTS

| | | | | |
|---|---|---|---|---|
| 2012/0178110 | A1* | 7/2012 | Zhang | C07K 16/283 |
| | | | | 530/387.3 |
| 2019/0259470 | A1* | 8/2019 | Olafson | G16B 20/50 |
| 2021/0174909 | A1* | 6/2021 | Rothberg | G16B 35/10 |
| 2021/0256394 | A1* | 8/2021 | Tymoshenko | G06N 7/005 |

OTHER PUBLICATIONS

Sortaller: predicting allergens using substantially optimized algorithm on allergen family featured peptides. Lida Zhang et al., Bioinformatics. Aug. 15, 2012;28(16):2178-9.

Enzyme-Based Strategies for Structuring Foods for Improved Functionality. Zeeb B, McClements DJ, Weiss J. Annu Rev Food Sci Technol. Feb. 28, 2017;8:21-34.

Written opinion of the ISA, PCT/US2022/021316, dated Jun. 2, 2022.

Patent drafting for machine learning. MD Stein et al., WSPLA presentation Sep. 18, 2019.

Highly accurate protein structure prediction with AlphaFold. Jumper J, Nature. Aug. 2021;596(7873):583-589.

Different Folding States from the Same Protein Sequence Determine Reversible vs Irreversible Amyloid Fate. Cao Y et al. J Am Chem Soc. Aug. 4, 2021;143(30):11473-11481.

Learning the molecular grammar of protein condensates from sequence determinants and embeddings Kadi L Saar et al. Proc Natl Acad Sci U S A. Apr. 13, 2021;118(15).

Clustering huge protein seguence sets in linear time. Steinegger M, Söding J. Nat Commun. Jun. 29, 2018;9(1):2542.

* cited by examiner

SYSTEM FOR IDENTIFYING AND DEVELOPING INDIVIDUAL NATURALLY-OCCURRING PROTEINS AS FOOD INGREDIENTS BY MACHINE LEARNING AND DATABASE MINING COMBINED WITH EMPIRICAL TESTING FOR A TARGET FOOD FUNCTION

REFERENCE TO EARLIER APPLICATION

This patent disclosure claims the priority benefit of U.S. provisional patent application 63/163,949, filed Mar. 22, 2021. The priority application is hereby incorporated herein by reference in its entirety for all purposes.

FIELD OF THE INVENTION

The technology disclosed and claimed below relates generally to the identification of natural sources of new food ingredients. It combines the fields of computer prediction and learning of structural and functional characteristics of biomolecules, rapid-throughput production of previously uncharacterized proteins, and assays related to physicochemical and sensory characteristics of proteins that are desirable for food products.

BACKGROUND

Agriculture has an enormous environmental footprint, playing a significant role in causing climate change, water scarcity, air pollution, land degradation, and deforestation. The global food system accounts for about 37% of greenhouse gas emissions. Seven percent of global freshwater is currently used for agriculture. By 2050, the global population is expected to grow to over 9.7 billion people. There is not enough clean water and arable land to meet increasing demands of the global population.

According to a recent authoritative report published by the World Bank and United Nations, continuing to feed the world's population at this pace until 2050 will clear most of the world's remaining forests, causing extinction of thousands of species, and releasing enough greenhouse gas emissions to exceed the 1.5° C. and 2° C. maximum warming targets in the Paris Agreement—even if emissions from all other human activities were eliminated. There is an urgent need to change current approaches to agriculture and food marketing to emphasize food products that are both sustainable and nutritious.

SUMMARY

This disclosure provides a technology for developing alternative protein sources for use in industrial food production. Shim, Inc. has built a thriving business from the idea that ingredients currently used in commercial food products can be substituted with proteins having known structure, but not previously known to have a desired target function.

For decades, the pharmaceutical industry has mined rich biologically diverse environments (tropical rainforest canopies and sea bottoms) to discover natural but previously unidentified small molecules that work as antibiotics or have other therapeutic impact. The technology described here is built on the same premise of mining natural sources—except that the mining is done partly in silico.

Instead of sampling and testing a vast library of compounds from a distant or wide-ranging environment, this technology narrows the field of functional candidates by predictive functional modeling drawn from known protein structure. Protein candidates selected in this way can be screened rapidly by recombinant expression and empirical testing to determine whether they have a target function and are suitable for further development as food ingredients.

Some of the Features of the Technology Put Forth in this Disclosure

This disclosure provides (among other things) a discovery method for identifying and developing proteins for use in manufacture of a combined product.

First, a computer system that is adapted for machine learning is trained to group similar proteins together and/or predict whether a protein has a preselected target function, wherein the target function is chosen based on the field of endeavor of the project. The ability of a particular protein to perform a desired target function may be predicted by the computer from one or more structural and/or functional characteristics of the protein, including at least the protein's amino acid sequence. Additional structural characteristics may include three-dimensional protein structure obtained from crystallography data, or predicted from the protein's amino acid sequence. Other functional characteristics may include molecular weight, charge, isoelectric point, solubility in aqueous solution, hydrophobicity, and binding affinity for other proteins or protein classes.

The computer system is trained by a process of machine learning that comprises inputting into the computer system a training data set that contains said characteristics for a plurality of proteins known to have the target function, and that also contains said characteristics for a plurality of proteins known not to have the target function.

Following the training, the computer system is applied to a source data set (such as a database consisting of or containing likely candidates). The database may contain mostly "naturally occurring" proteins, which means proteins that can be identified in biological sources in nature, or can be isolated or otherwise obtained from biological sources without recombinant DNA technology. The database includes structural and other characteristics for each protein it contains, including at least each protein's amino acid sequence.

The trained computer system assesses proteins in the database, and compiles a list that identifies or ranks protein candidates that are predicted (but typically not already known) to have the target function. Characteristics analyzed in the training in step and/or included in predicting target function may include a homolog comparison for similarity of one or more of the following structural features in any combination: protein amino acid sequence, protein three-dimensional structure (obtained from crystallography data or predicted from the protein's amino acid sequence), vector representations of physicochemical and biochemical properties of amino acids and/or clusters of amino acids in each protein, optionally combined with vector representations of properties of the protein as a whole.

Empirical evaluation is done next. The protein candidates on the computer-generated list are recombinantly expressed and purified in a high throughput manner. This can include expressing each protein with a tag, and using the tag for affinity purification using a conjugate binding partner. The isolated proteins are then assayed to determine or quantify which of the expressed protein candidates actually have the target function. The expressing and purifying may be repeated one or more times to improve volume and/or quality of protein production. The expressing, purifying, and assaying is generally done in a manner that promotes high-throughput screening. Besides the ability of expressed protein to perform the target function, the empirical evaluation may include determining or measuring other features, such as physicochemical properties selected from thermal stability, buffering capacity, solubility, and charge.

One or more of the expressed protein candidates that are determined to have the target function above a certain threshold or at a satisfactory level are then selected for further workup. This would include additional tests to determine whether the protein meets desired performance requirements when placed in the context of its intended purpose. For industrial production, the protein may be isolated from a natural or agricultural source, or produced recombinantly in a different system than the process used for high-throughput evaluation.

The computer prediction and empirical screening can be done in an iterative or cyclical fashion, wherein the structural data and/or assay results for the protein candidates that have been tested are added into the training data set. One, two, or more than two additional cycles of the predicting, expressing, and testing can be done until a desired number of potential food ingredients for the intended use have been selected. If the number of potential ingredients obtained in a single pass-through of the predicting, expressing, and testing is sufficient for the user's purposes, then additional iterations are optional. Once the number of potential ingredients for the intended purpose has been obtained, each protein is typically manufactured in its intended context or a proxy thereof to determine whether it meets desired performance requirements.

Depending on the field of use and objectives of the user, the technology can optionally be implemented without machine learning and/or without reiteration. In some contexts, technology can also be implemented without using homology comparison of primary amino acid sequence data as the primary focus. Instead, the comparison is done by comparing proteins in a database with proteins known to have a target function using three-dimensional protein structure, and/or vector representation of structural and three-dimensional features of individual amino acids and clusters thereof. This helps identify candidates that may have the target function because of a shared core structure and even if they don't share primary sequence homology with proteins known to have the target function.

For example, potential food ingredients from natural sources can be identified by accessing a database that contains amino acid sequence data of naturally occurring proteins. A plurality of the proteins in the database are encoded as a vector representation of physicochemical and biochemical properties of amino acids and clusters of amino acids (typically using artificial intelligence in an appropriately programmed computer in combination with input from the user). The vector representations of proteins in the database are then compared with vector representations of proteins known to have a desired target function. Alternatively or in addition, known or predicted three-dimensional structure of proteins in the database are compared with proteins known to have the desired target function. Naturally occurring proteins in the database are thereby identified and/or ranked according to whether they are predicted to have the target function, thereby obtaining a set of protein candidates.

The candidates are recombinantly expressed and purified, and then assays are conducted to determine or quantify which of the protein candidates actually have the target function. Based on the assay results, one or more of the expressed protein candidates may be characterized as potential food ingredients. The potential ingredients are then tested to determine whether they meet desired performance requirements as part of a food preparation. Optionally, the data obtained from the assays is used to adjust the encoding and/or weights of feature vectors of proteins in the database into vector representations, and the steps of comparing, expressing, and assaying are reiterated to obtain additional potential food ingredients. Optionally, the encoding of the proteins is repeated and optimized by the assistance of machine learning and/or user input.

The various procedures and steps of the discovery system need not be done in a particular order unless explicitly stated or otherwise required. Often, results of the empirical evaluation will be used to help train the computer system on an ongoing basis, and the computer system will continue to mine databases in an ongoing manner to nominate additional proteins to the list of proteins predicted to have the target function.

Applications of the Technology

These discovery methods of computer prediction, expression, and screening can be used for identifying ingredients for food preparations having a desired property, for the purposes of introducing the property into the foods, or substituting or supplementing for another protein (potentially from an animal source) that is more traditionally used in such foods. The same discovery methods can also be applied to the discovery and development of proteins for use in other fields of manufacture, as described in the description that follows.

Presence of species homologs in a protein database may skew the list of protein candidates selected by the computer in favor of protein classes having a relatively large number of species homologs in preference to other protein candidates. For purposes of compiling an initial list, the user may decide to remove or downgrade proteins identified as species homologs and/or isoforms from the set of protein candidates, either in a supervised or unsupervised manner. Subsequently, for purposes of selection refinement, the user may decide to focus the computer selection criteria on homologs of a protein that has been evaluated empirically as having promise for further development, thereby optimizing the choice of which homolog should be used for ultimate workup.

In some instances, a function that is predicted to be present in a protein by computer analysis may not be evident in empirical testing. This means that the function is potentially present but "masked" (hidden) within the protein stochiometrically or by other means. In this situation, development, assessment, and ultimate selection of a protein candidate may include unmasking the target function. The unmaking may be done by recombinantly expressing and purifying a potentially unmasked version of the protein in which a part of the protein predicted to have the target function is excised from other parts of the protein that are believed to mask the target function, and then conducting additional assays to determine or measure whether the potentially unmasked version of the protein has the target function. The protein expressed for testing or ultimately selected for the intended propose may be a truncated version of the naturally occurring protein, or a fusion protein containing the naturally occurring protein or a truncated version thereof.

The discovery method may also include selecting proteins in the computer prediction phase, or selecting promising candidates following empirical assessment based on other desirable features beyond ability of the protein to perform the target function. Positive selection criteria may include solubility, ease of expression, ease of purification, stability on storage, and mixability. Negative selection criteria may include potential toxicity and adverse environmental effects. Such criteria may be predicted by computer algorithm in the process of candidate ranking, and/or determined in the empirical evaluation, in any combination.

The discovery system of this disclosure may be put to use to identify potential food ingredients for any suitable purpose. Reasons for using this system may include replacing an animal or unsustainable sourced of a food ingredient with a suitable substitute, or to confer or augment a particular function or property to improve a food product.

In this context, the target function may be selected from antimicrobial activity, gelation, moisture retention, fat structuring, adhesion, fiber formation, particular flavors, and other functions referred to below. Additional positive selection criteria may include one or more desirable flavors or sensory properties, such as texture and mouth-feel. Negative selection criteria may include allergenicity or immunogenicity, incompatibility with other food ingredients, an adverse physiological effect, and an undesirable flavor. The empirical evaluation may include properties such as emulsion stability, foam stability, gelation, chewiness, storage modulus, water binding capacity, swell ratio in water, sedimentation rate, adhesiveness, antimicrobial activity, and enzyme activity.

Performance requirements of potential food ingredients used in the ultimate workup may include sufficient activity of the target function by the potential food ingredient when compounded into a food product, and compliance of the food product with regulatory requirements.

This disclosure provides a method of preparing a food product containing a protein not previously used as a food ingredient, selected and evaluated by the discovery system put forth above. A conventional food ingredient may be replaced with a protein identified by the discovery system, for example, by identifying one or more target properties of the conventional food ingredient to be replaced, and then preparing the food product in which a food ingredient identified and developed according to the discovery system as having said target properties replaces the conventional food ingredient. The disclosure also provides food products prepared that incorporate proteins selected and evaluated by the discovery system put forth above.

Additional aspects, embodiments, features, and characteristics of the invention, its products, their manufacture, and use are described in the sections that follow, the accompanying drawings, and the appended claims.

DETAILED DESCRIPTION

The food ingredient discovery process provided in this disclosure uses computer-driven modeling that predicts protein function from structure information available in protein databases. Candidate proteins are produced and tested empirically by a high-throughput process to determine if they have a target function and other desirable properties that exceed a desired threshold or benchmark. Promising candidates are then nominated for further development as replacement or supplemental ingredients for inclusion in commercially produced food products.

Advantages of the Technology

There is considerable interest in the food industry in developing new food sources that consume fewer resources and lessen environmental impact. Extensive research is under way in the use ingredients produced in plants and in cell culture. Unfortunately, plant-based products typically lack the likeability of traditional ingredients because they don't taste, feel, or behave like the animal or chemical products they are replacing. If we can identify naturally occurring ingredients that can overcome these deficiencies or find superior products that perform better than traditional ingredients, then environmental objectives can be met while improving and enriching the consumer's dining experience.

The ingredient discovery and development technology put forth in this disclosure has several major advantages over earlier approaches:

Potential sources of natural food ingredients are not limited to a particular catalog of plant products. Since any protein database can be sourced by computer for initial screening, potential sources are limited only by the extent of publicly available knowledge of structurally characterized proteins.

Prediction of protein function is not limited to a simple sequence alignment. By integrating machine learning, vector representation of protein features, and laboratory assays, the system learns on an ongoing basis what features are important for a particular target function—thereby providing a wide range of suitable candidates.

Using high-throughput expression and laboratory analysis as part of the learning process anchors the search process in real-world effectiveness. This enables the user to survey widely for candidate proteins, and thereafter to narrow the list of candidates for final workup. As a result, ideal food ingredients are identified and characterized to meet particular objectives.

The ability to iteratively source and test proteins from a wide range of databases is a superior approach for obtaining ingredients from non-animal sources that mimic culinary and sensory properties of animal sourced ingredients they are replacing.

Iterative Prediction and Testing of a Target Protein Function

Figure 1:
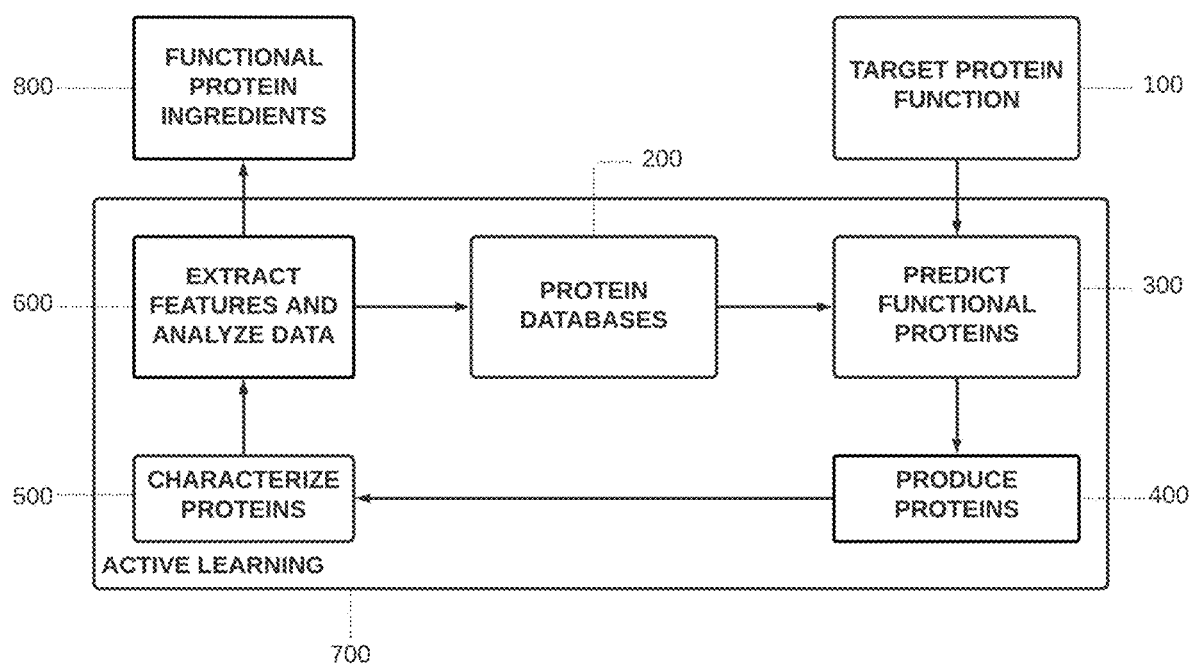
FIG. 1 depicts a discovery flywheel that can used in accordance with this disclosure for identifying new food ingredients 800 with a target function 100. The discovery system uses repeated cycles of machine learning 700 to mine protein databases 200 for candidate proteins 300 predicted to have the target function, which are then produced 400 and empirically characterized 500. Results of the testing 600 are used to nominate promising candidates for further testing as food ingredients 800. The data also feeds back as part of active learning to enhance mining of the protein databases 200 and prediction of functional proteins 300 in the next iteration of the cycle.

FIG. 1 is a flowchart that represents an overview of an iterative system of procedures and events that can be implemented in accordance with this technology.

The user selects a target protein function 100 for a new food ingredient at the outset to guide the discovery process. Selection of the target protein function may be inspired by one or more hypotheses that explain in part how physico-chemical properties of proteins influence protein function. These hypotheses may be used to guide curation of the data.

Data processing includes curation of one or more databases 200 that contain relevant information on protein structure and characteristics for use both for computer training and as a source of new ingredients. These databases may include information from public protein and genomic databases, metadata obtained through partnership with other institutions, and/or internal or proprietary information, such as may be obtained empirically from previous test data or predictions of protein characteristics and performance.

One or more protein functions are predicted 300, and candidates are selected using a combined approach of machine learning and traditional bioinformatic analysis. The output of this process is a set of candidate proteins, which may be ranked in terms of degree of target function or a combination of desirable features. The number of proteins selected is typically limited by the capabilities of the laboratory to produce and characterize the candidate proteins in each cycle of the discovery process.

After selection, candidate proteins are produced 400 and purified for testing. For purposes of rapid screening of candidate proteins, the selected proteins are typically produced by recombinant expression by transforming or transfecting a host cell line or system with a polynucleotide encoding each candidate. Proteins predicted to have the target function and recombinantly expressed are then characterized 500 for the target function 100 and potentially for other physicochemical and/or functional characteristics. Raw data generated by the analytical measurements performed while characterizing proteins is processed to extract important features 600 to help assess performance.

Evaluation of the ability of candidate proteins to perform the target function 100 may be assessed against the performance of various ingredient benchmarks or other known functional proteins within the database. If a protein fails to meet the desired performance goals, its data is still added back into the internal protein database to retrain the system, improving the ability to predict and mine functional proteins 300 with the target function 100 in subsequent rounds of discovery by active machine learning. If the protein does meet the performance requirements, it may be nominated to continue development. The nominated proteins are tested as ingredients of trial food products 800 to determine whether they may be used for commercial manufacturing.

Unmasking Hidden Function

The food ingredient discovery process described here uses proteins from natural sources in new ways. The technology put forth in this disclosure derives much of its power from its ability to discover and develop properties that were not previously appreciated for known proteins. The owners of this technology believe there is a bounty of proteins with hidden function that can be culled as useful food ingredients, revamping the food production and marketing business.

Some functions of naturally occurring proteins may have previously been unknown for any of several reasons:

1. The natural source of a protein with the target function may not be something that is traditionally considered as a source of food ingredients;
2. Concentration of the protein in its natural source may be too low for its properties to have been demonstrated in the normal course of food product development;
3. The protein function may be shrouded in its natural context by other components that have a different or more pronounced property; or
4. A part of a naturally occurring protein having the target function may be masked within the structure and function of the rest of the protein.

The technology described in this disclosure is suited to discover protein function that has previously been hidden in any of these ways. In FIG. 1, using a protein sequence database 200 as a source of candidates overcomes the first two of these obstacles, because it reaches beyond sources of traditional foodstuffs and brings to the fore any proteins that are predicted to have the target function, regardless of its natural source and concentration. The third obstacle is overcome at the production stage 400 by recombinant expression of the protein for purposes of characterization 500. There is no need to purify a promising candidate from other constituents of its natural source that confound testing. Instead, the candidate protein needs only to be isolated from the host cells and other constituents of the culture broth, which is a routine matter for most candidates produced in established culture conditions.

Dealing with the fourth obstacle requires unmasking a promising part of a complex protein from the rest of the protein. This is suggested where a candidate protein scores highly in the prediction stage 300 but shows very low target function in the characterization stage 500. The results of the prediction are analyzed further to identify what part of the protein is believed to have the target function. The expression vector is then adapted to trim the open reading frame at the 5' and/or the 3' end of the encoded protein so that the relevant part of the protein can be produced on its own, in the absence of other parts of the protein that prevent the target function from being manifest. The isolated portion or fragment of the protein is produced and purified 400, and retested in the characterization stage 500 for the target function and other desirable properties. Protein fragmentation and extraction can be done in this way not just to unmask or enhance the target function, but also to eliminate other unwanted characteristics or function, or just to reduce protein bulk.

Other alterations from the structure of a naturally occurring proteins are also permitted, if acceptable in the context of the intended use. Besides protein truncation or deletions, the protein may be adapted with one or more amino acid changes to create a variant of the naturally occurring protein or fragment thereof, thereby adding a desired property, removing an undesired property, or for any other reason. Such variants are typically at least 95%, 98%, or 99% identical in terms of amino acid sequence relative to the naturally occurring protein or a fragment thereof.

Alternatively or in addition, the user may use recombinant technology to build a protein candidate, fragment, or variant thereof having the target function into a larger fusion protein or protein assembly. The fragment having the target function is conjoined or coexpressed with one or more other proteins or fragments during recombinant expression. The other components of the fusion protein or protein assembly may be selected from proteins known to have other beneficial properties, or discovered by using the technology described here in search of the same or a different target function.

Exemplary Target Functions

The technology of this invention can be used for the purpose of identifying replacement ingredients that are more desirable in food products for one reason or another, replacing an ingredient that is traditionally used in a food recipe or formula, but for one reason or another should be replaced. Ingredients may be more desirable—for example, because they are obtainable from a more sustainable or environmentally friendly form of architecture or harvesting, because they are less expensive to produce, or because they have other beneficial characteristics. Once an ingredient in a foodstuff is selected for replacement, the user identifies a target protein function 100, which becomes the object that guides the iterative process shown in FIG. 1.

Exemplary target functions include the following: gel-forming properties; foaming agents; carriers for flavor, color, vitamins, porphyrin, heme, or carbohydrate; moisture retention; antimicrobial activity and other preservation functions; fat structuring (for example, for oleogel creation); adhesive and film forming agents; ingredients with enzymatic or hormonal function; emulsifying agents; nutritional supplementation (such as casein); viscosity alteration or moisture retention; agents that cause flocculation or adhesion; fiber; and structural components that support scaffolds.

By way of example, the ingredient discovery system put forth in this disclosure can be focused on gelation as a target function. The objective would be to identify a high strength gelling agent, similar to egg white protein, that is non-allergenic, designed to bind ingredients at low concentrations, and suitable for cooking. Egg is frequently used as a binding or gelling agent to hold other ingredients together in foods like processed meat products, baked goods, and confectionary. Egg components are also used in many alternatives to processed meat, including vegan equivalents of sausages and meat patties. Currently, egg ingredients are relatively inexpensive, whereas plant proteins that promote gelation are in relatively low abundance in agricultural products, making them difficult and expensive to use as substitutes. A more easily sourced protein having suitable gelation properties is desirable to replace egg in many food products. Finding a naturally occurring gelation substitute that can be easily purified or produced recombinantly would transform the way many of these foods is made.

Source Databases

The information databases 200 used as a potential source of data for proteins having the target function generally come in two forms: public databases, including information such as protein amino acid sequence and crystal structure, and possibly other protein characteristics such as physico-chemical properties and natural sources. There may also be an internal database that collects information not only on protein structure, but also physicochemical and functional characteristics that are tested or assessed as part of the protein discovery process.

Figure 2:
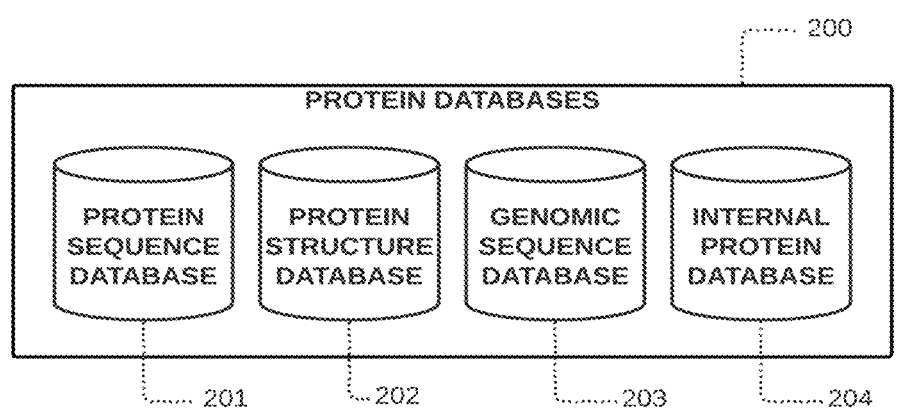
FIG. 2 shows several types of protein databases 201, 202, 203, and 204 that may be sourced for training data and as a resource for discovering and predicting new food ingredients that have a target function.

FIG. 2 shows an arrangement of databases that may be used as information sources for the protein discovery process. Protein sequence databases 201 typically contain information related to the amino acid sequence of the protein, including alternative isoforms and sequence variants. The sequence databases may also contain functional annotations about the protein, including its primary function, source organism, cellular component, and metabolic pathways. Exemplary protein databases are UniProt/SwissProt, UniProt/Trembl, PFAM (a database of curated protein families, each of which is defined by multiple sequence alignments and a profile hidden Markov model), ProteinNet, Uniparc, and Uniref90.

Protein structure databases 202 typically contain information on the three-dimensional configuration of proteins that define their secondary, tertiary and quaternary structure, gathered from such techniques as X-ray diffraction, nuclear magnetic resonance, and cryo-electron microscopy. Detailed information may include atomic-level coordinates and amino acid level assemblies. Local structure data may include features such as alpha helices and beta sheets. Exemplary structural databases include the Protein Data Bank (PDB), the Structural Classification of Proteins database (SCOP), the Pfam database, and the CATH Protein Structure Classification database.

Genomic sequence databases 203 contain nucleic acid sequence information organized at the organism, chromosome, gene, and transcript level. Besides the encoded protein, genomic sequence databases contain information that is upstream or downstream from the reading frame, and in introns. Genomic sequence data can be used computationally to infer multiple open reading frames or multiple isoforms of the same protein. Exemplary genomic or nucleic acid sequence databases include MI Phytozome, NCBI Refseq, NCBI Genome, and the Plant Genome Database (PGDB).

The internal protein database 204 may contain structural data for proteins, and information generated experimentally from protein selection, expression, purification, and characterization.

In the context of machine learning and data mining in accordance with this disclosure, general reference to a protein database or an informational database may refer to any one of these databases or a selection thereof in any combination.

Predicting Protein Function

Protein information sourced from the databases is analyzed by computer to predict whether each protein in the databases or a selection thereof have the target function.

Figure 3:
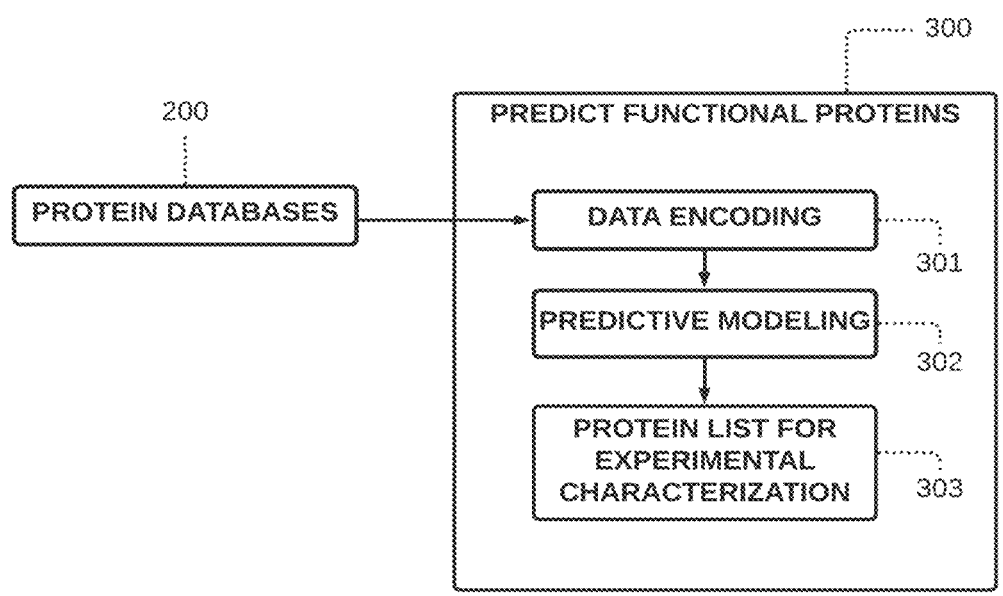
FIG. 3 shows how a computer system can use predictive modeling 302 of encoded data 301 to identify and select protein candidates 303 for experimental characterization.

FIG. 3 shows steps typically used in the process of predicting and identifying functional proteins 300. The computer system performs data encoding 301 and predictive modeling 302. This produces a list of candidate proteins 303 for experimental characterization.

The data is encoded 301 in vector or matrix form to be processed by the machine learning models. Continuous features can be normalized and/or discretized. Categorical features are one-hot encoded, binary encoded, or hash-encoded. Protein amino acid sequences can be transformed so that the dimensionality of the space they are lying in is reduced. Sequences and additional features for protein of various lengths are encoded in a fixed sized matrix. This is done with word-bagging, with autoencoders or with encoder-decoder models such as Seq2seq (Sutskever et al., arXiv:1409.3215, 2014) or Transformers (Vaswani, et al., arXiv:1706.03762, 2017). Models that generate embeddings (a fixed size vector representing a sequence or a single residue) are trained on large amounts of unlabeled data.

Input data for predictive modeling may include one, two, three, or more than three of the following features for each protein, sourced from one or more databases:

amino acid sequence;

three dimensional structure, obtained from crystallography data, predicted algorithmically from a protein's amino acid sequence (for example, using AlphaFold 2.0™, AW Senior et al., 2020, Nature 577 706-710), or obtained from a three-dimensional database (such as the AlphaFold™ Protein Structure Database from Google's DeepMind and EMBL-EBI);

residue-level features, encoded as a set of vector representations for physicochemical and structural features of each amino acid and/or clusters of two or more amino acids that are proximate to each other in sequence or in three-dimensional space, typically predicted from amino acid sequence;

protein level features encoded for the protein as a whole (such as amino acid length, overall charge, hydrophobicity, presence of structural features such as alpha helices and beta-pleated sheets, and protein crosslinks), predicted from amino acid sequence, three dimensional structure, or determined empirically; and results from empirical assays done as part of the high-throughput expression and screening during the discovery process.

Residue level features can be sourced using AAindex, a database of numerical indices representing various physicochemical and biochemical properties of amino acids and pairs of amino acids. There are three sections: AAindex1 for the amino acid index of 20 numerical values, AAindex2 for the amino acid mutation matrix and AAindex3 for the statistical protein contact potentials. All data are derived from published literature. S. Kawashima et al., Nucleic Acids Res 2008; 36:D202-5.

Input data in each category can be categorical, or continuous. Categorical data is defined as variables that contain labels instead of numerical values. Examples of protein categorical data are protein family, cellular location, and source organism. Depending on the nature of a target function or a protein characteristic, the feature may be coded as a categorical variable or a continuous variable. Categorical data are defined as variables that contain labels instead of numerical values. Examples of protein categorical data are protein family, cellular location, and source organism. Continuous or numerical data are values that are composed of numbers. Examples of protein continuous data are molecular weight, isoelectric point, and percentage of each amino acid type.

Figure 4:
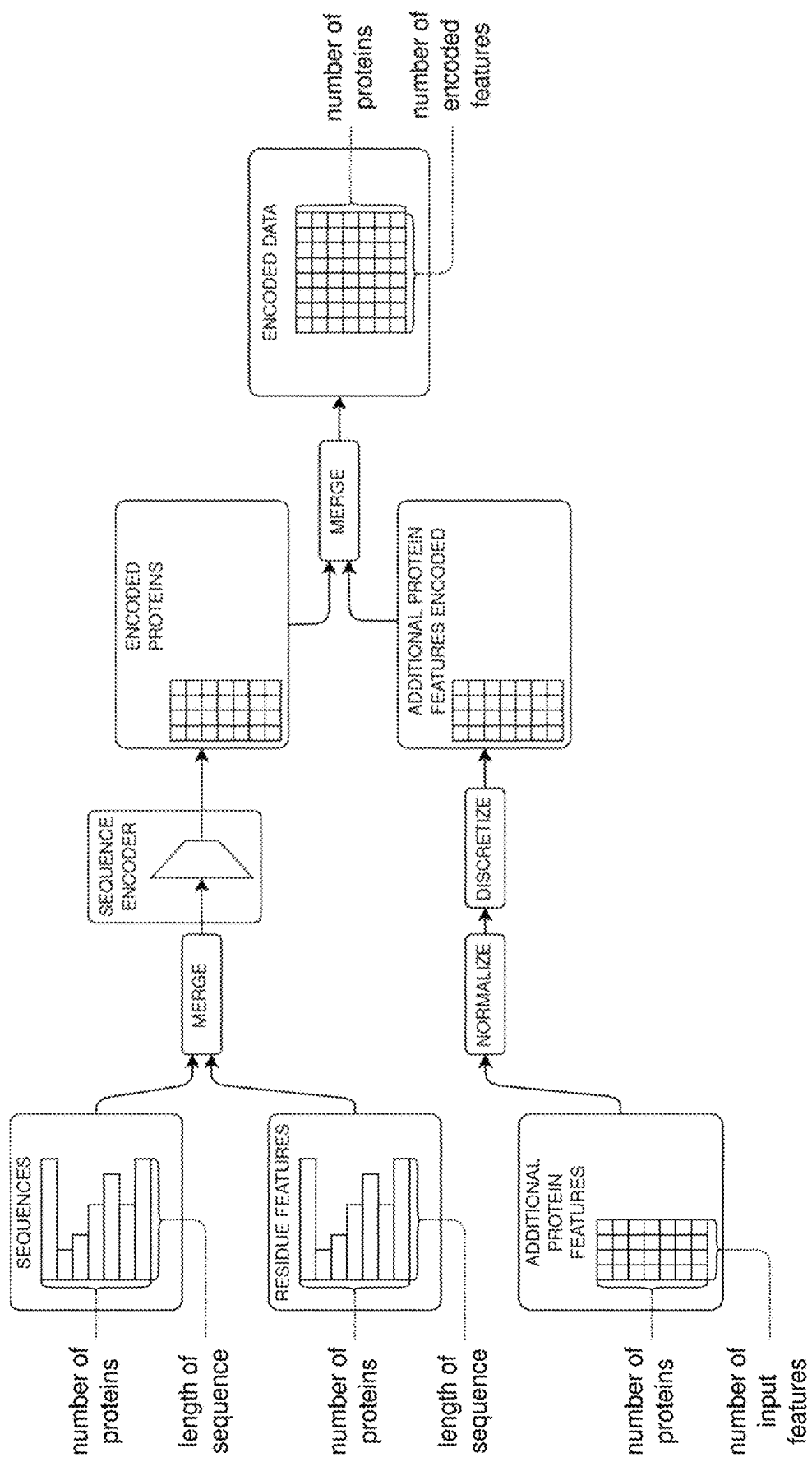
FIG. 4 shows the encoding of sequence data and protein characteristics for training and analysis by the computer system.

FIG. 4 shows a suitable data encoding process. Sequences, residue level features, and protein level features are merged and encoded. The encoder learns how to represent features of a protein in a compressed space in a way that it can be reconstructed and compared with data from other proteins. Additional protein features for each protein are normalized and discretized, and merged into the encoded data.

In situations where only a few data points are labeled out of a larger ensemble, a process of active learning or retraining may be used to drive the labeling of new data. Iteratively, given a predefined query strategy and model behavior on labeled data, new data points are picked for labeling and the model parameters are updated. In practice, this means augmenting the current dataset with new proteins that are less likely to perform well given the current model (for example, representing groups with higher misclassification or higher uncertainty).

The training or test data set is constructed as follows. Proteins sequences contain regions of variable conservation due to selective pressures on random amino acid changes. Therefore, their sequence is not independent and identically distributed (IID). Since IID is a requirement for train-test splitting and cross-validation (CV), proteins are clustered according to their sequence or MSA similarity first. Then the clusters are shuffled, and a split is performed among the clusters.

Figure 5:
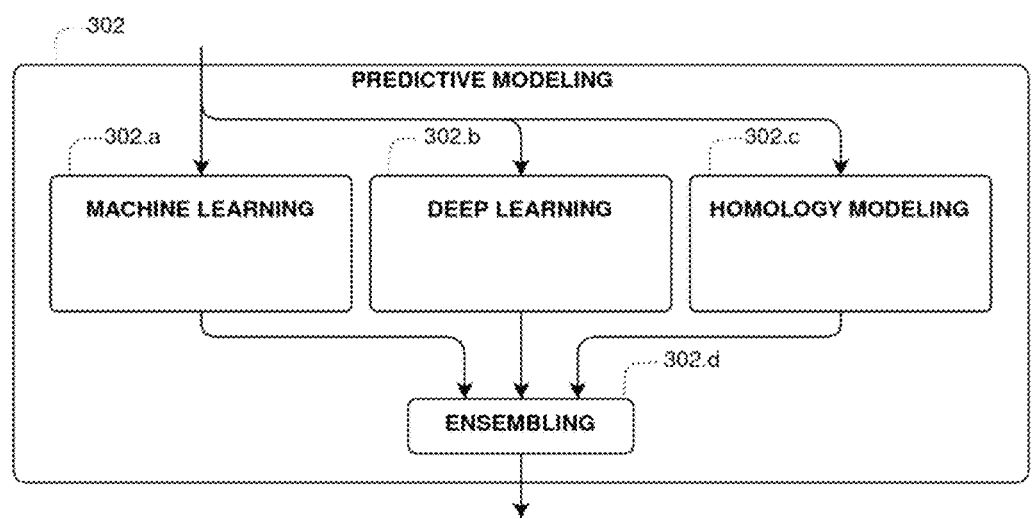
FIG. 5 is a chart that shows different types of computer processes 302*a* to 302*d* that can be used as optional components of machine learning for predicting protein function.

FIG. 5 shows various types of machine learning that can be brought to bear for predictive modeling 302.

Machine learning (ML) 302a is a method of data analysis done by computer that automates analytical model building. It is a branch of artificial intelligence based on the idea that systems can learn from data, identify patterns and make decisions with minimal human intervention. T. Mitchell, Machine Learning. New York: McGraw Hill, 1997.

The paradigm of machine learning 302a incorporates two phases: the training phase and the inference phase. During the training phase, protein sequences, residue level features, protein level features are provided to the model as input. Additionally, protein targets are provided to the pre-defined loss of model. The loss function calculates the loss used by the optimizer to update the model parameters iteratively until convergence. The result of this operation is a set of fixed parameters that are used at inference time. The sequences and features at residue and protein levels are generated the same way at inference time as during training.

For protein features that are categorical, the prediction task is classification, classification losses (e.g., cross entropy) and metrics (e.g., AUROC). For example, if the target function is gelation, a binary category may be used depending on whether a particular protein gels or not. For protein features that are continuous (such as degree or scope of antimicrobial activity), the prediction task is calculation of regression losses (e.g., MSE) and metrics (e.g., $r^2$). Using the example of the gelation property, the function can be defined using a value $x=\{0, 1\}$, where $x=0$ represents the absence of any gelling while $x=1$ represents the highest measured gelling value observed. The regression task is to predict the continuous value of x for a new protein.

Deep learning (DL) 302.b may also be used for predictive modeling. Deep learning is a class of machine learning algorithms that uses multiple layers to progressively extract higher-level features from the raw input. Each level learns to transform its input data into a slightly more abstract and composite representation. Bengio et al., IEEE Transactions 35: 1798-1828, 2013; Deng et al., Foundations and Trends in Signal Processing. 7: 1-199, 2014; Lecun et al., Nature. 521: 436-444, 2015. DL is a sub-ensemble of the machine learning techniques, using different architectures, more model parameters, and allowing for unstructured input data. It relies on the successive application of differentiable transformations on the input data. The sequence of transformations defines the architecture of the DL model (for example, convolutions, pooling, and rectifier are the transformations that define Convolutional Neural Networks (CNN)).

Homology modeling 302.c leverages bioinformatics tools that can compare genes, transcripts, and proteins to identify similar entities which may share common functional characteristics. Proteins that share similar sequence, structure, and family annotations can be inferred to serve similar functions in the context of food ingredients. One such example is the BLAST (basic local alignment search tool) software provided through the National Center of Biotechnology Information that can find regions of nucleic acid or amino acid homology between a target sequence and databases of query sequences. Since homology modeling methods do not require experimental data generated in the internal protein database, these analytical tools can be applied before proteins are produced for empirical testing.

Combinations of these and other forms of machine learning may be referred to in this disclosure as hybrid or multimodal machine learning. Baltrušaitis et al., arXiv: 1705.09406v2, 2017.

The ensembling process 302.d takes as input the predictions of the other models (302.a, 302.b, 302.c). In practice, ensembling performs a weighted average of predictions of protein function that are made in different ways. The set of weights (for the average) is optimized to minimize a pre-defined loss function on a set of unseen data points. Those weights can be arbitrarily defined to give more or less prediction power to each of the models used based on an expert's input.

The output of the predictive modeling 302 is a list of proteins 303 that is potentially ranked or sorted by relevance to the target protein function, optionally influenced by other desired features. The chosen proteins or a subset thereof is subsequently characterized by a plurality of criteria tested in different assays. Each criterion may be considered to have high, neutral, and no relevance to the target protein function. The high relevance criteria likely yield functional proteins suitable for further workup. The neutral and no relevance criteria generate data that can be used for the purpose of refining the predictive models in further cycles of active learning. The machine learning may be set to group similar proteins together; and/or to predict protein function from structure and other characteristics.

Protein Production

Figure 6:
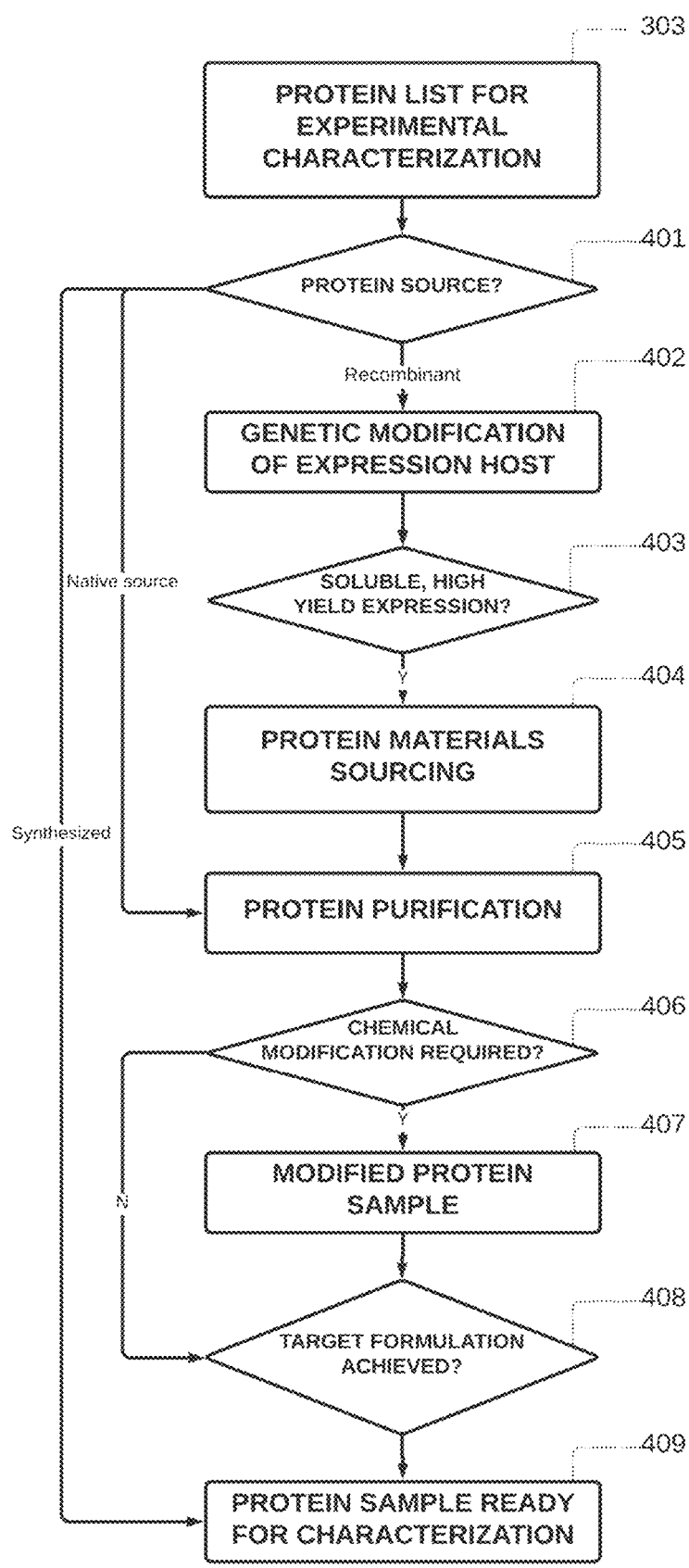
FIG. 6 shows the process flow by which candidate proteins may be sourced 404 and purified 405 for empirical characterization 409.

FIG. 6 is a flow chart that outlines a process by which proteins selected from the list generated in silico 303 may be produced for empirical testing. A decision is made 401 as to the source and mode of production: either from natural sources, by recombinant expression, or by chemical synthesis. If proteins are obtained from a native source, they pass directly to the purification step 405 while recombinant proteins are made in the expression stage 402. If the sequence of a protein or peptide is short and does not require modifications, the protein may be produced by solid-phase synthesis, whereupon they pass directly to characterization 409.

Amongst these choices, recombinant protein production is typically used for high throughput screening, allowing a list of proteins to be assessed at the same time in the same way. Recombinant production is done by genetic modification of an expression host 402. Cell lines (cultures of animal cells), microorganisms (yeast, fungus, or bacteria), plants (such as algae or wheat), or cell-free extracts (for example, that contain material extracted from expression-competent cells) may serve as a host. The host is genetically modified (through infection, transformation, or transfection) to integrate DNA or carry plasmids designed to express the protein of interest constitutively or via induction. Genetic modification may also include the use of sequences that modify the protein by adding DNA that encodes for peptide or small auxiliary protein tags. The tag can be used for downstream purification and characterization. Reference books on the subject include *Recombinant Gene Expression*, A. Lorence ed., 2012; New *Bioprocessing Strategies*, B. Kiss et al. eds., 2018; and *Cell-Free Synthetic Biology*, S. Hong ed., 2020.

Suitable organisms used for recombinant expression of candidate proteins are listed in Table 1. Host organism selection is done taking into consideration the ability for the host to express soluble protein in high quantities with the post-translational modifications (such as addition of carbohydrates and/or interchain crosslinking) that may affect protein function.

TABLE 1

Recombinant expression systems for candidate proteins

| Organism | Strain |
| --- | --- |
| animal | *Drosophila* S2 |
| animal | SF9 |
| animal | SF21 |
| animal | CHO |
| yeast | *Pichia pastoris* (*Komagataella phaffi*) |
| yeast | *Saccharomyces cerevisiae* |
| filamentous fungi | *Aspergilllus* |
| filamentous fungi | *Trichoderma reesi* |
| filamentous fungi | *Neurospora crassa* |
| bacteria | *E. coli* |
| plant | *Nicotiana benthamiana* |
| plant | *Solanum lycopersicum* |
| algae | *Chlamydomonas reinhardtii* |
| cell free | plant extract |
| cell free | bacteria extract |
| cell free | yeast extract |

Eukaryotic expression systems have the advantage of performing post-translational processing of protein candidates in a manner akin to what may be used naturally or for industrial production, such as glycosylation and interchain crosslinking Prokaryotic expression systems have the advantage of being easy to implement and obtain high yield. It is possible to use several systems during development: for example, expression in *E. coli* for performing screening assays; and expression in eukaryotes for later stage development and testing. Some expression systems such as yeast are suitable for use in both stages.

The expression product is evaluated 403 for solubility of the protein and yield. Proteins are preferably water or buffer soluble and expressed at high enough yields to be used for downstream characterization. Solubility and expression data on a specific protein may be used to evaluate the potential for a protein to be generated in larger quantities. Techniques such as gel electrophoresis, capillary electrophoresis, and ELISA can be used to determine the presence of a tagged protein, check molecular weight of the protein, and provide yield evaluation. Protein solubility can be tested by fractionation using filtration, gravity, or centrifugation followed by analysis of the soluble aqueous phase to determine if the protein presence. The amount of soluble protein required from this step is dependent on the requirements for the biochemical and materials characterization, where specific assays selected depends on the target function of interest. If proteins achieve the solubility and yield criteria, they are then purified. If expression of a protein does not pass, the data is collected in the internal protein database for purposes of predicting other protein candidates and expression potential. Alternative expression systems may also be tested with a view to increasing yield if a candidate protein is considered promising for other reasons.

Materials for recombinant purification are sourced 404 from fermentation of host organisms using standard fermentative procedures such as plate, flask, or bioreactor fermentation. Natural source materials can be obtained from whole or isolated fractions from fungi or plants.

Protein purification 405 is optional if characterization assays do not require pure protein. For example, enzymatic activity of a protein may be assessed using a mixture of proteins and may not require purification. The purification strategy will vary depending on the source (native or recombinant) and the level of purity needed for characterization assays. Both recombinant proteins and native source proteins may be purified using standard purification procedures. Both recombinant and native sourced proteins can use methods for protein isolation including dry and wet processing.

Common purification methods include centrifugation, filtration, affinity chromatography, ion exchange chromatography, size exclusion chromatography, hydrophobic interaction chromatography, affinity capture, isoelectric precipitation, liquid-liquid phase separation (LLPS), lyophilization, and dialysis. One of these methods may be used as a single step or combined with other methods as needed to achieve a desired level of purity. Once achieved, the protein is processed by standard methods into a final condition that is compatible with characterization methods. For example, some assay methods may require powdered protein, while other characterization methods may require proteins in aqueous solution. Reference books on this topic include *Protein Purification,* 2nd Ed., P. Bonner, 2018; and *High-Throughput Protein Production and Purification,* R. Vincentelli ed., 2019.

To facilitate protein purification (particularly for high-throughput empirical testing of protein candidates), recombination protein can be expressed with an exclusive tag for affinity binding. In this context, a "tag" is any feature added to the protein during expression that can be used as a handle for affinity purification using a conjugate binding partner. Examples include amino acid sequences added internally or to either end of the naturally occurring protein sequence, and carbohydrates. By way of illustration, an additional sequence of amino acids (perhaps at least 5, or between 5 and 50, or 8 and 25 amino acids in length) can be included in the open reading frame (typically at the N- or C-terminus) that is recognized by a binding partner such as a conjugate receptor, antibody, or other binding protein. Another example is an embedded protein sequence that acts as a recognition site for carbohydrate-loading enzymes, creating a glycosylation feature that can be captured with a conjugate binding moiety such as a lectin.

Suitable protein tags include poly-histidine that binds to metals such as nickel, cobalt, or zinc, GST protein that binds to glutathione, and c-myc protein that binds to anti c-myc antibodies. Other alternatives area flag tag (the 8-amino acid sequence DYKD followed by DDDK) which is captured using anti-flag antibodies, or the CL7 tag, available from TriAltus Biosciences, which binds to an IM7 resin. After the tagged protein is immobilized on an affinity surface, fermentation byproducts can be washed away. Depending on the tag used, the purified target protein can then be eluted from the resin using competitive binding or a condition change, such as pH.

For purposes of initial screening, the tag can be left on the protein after purification, unless there is a concern that it might interfere with the functional assays. For later-state testing or preparing a finished product, the open reading frame may include a specific proteolytic cleavage site between the tag and the rest of the protein. A cleavage enzyme, such as tobacco etch virus (TEV) protease, can be incubated with the protein to remove the tag. The cleaved tag, any uncleaved recombinant protein, and the cleavage enzyme can then be removed by other means, leaving the purified target protein.

The next step 406 is to assess whether chemical modification is required. Purified protein samples may undergo chemical modification for certain target functionalities of interest. Modifications may include hydrolysis to produce protein fragments, crosslinking of proteins, or other enzymatic treatments. Chemical or enzymatic modification results in a modified protein sample 407, which is then evaluated for target metrics similarly to proteins that did not undergo modification.

Target formulation 408 of a protein preparation typically is a stable formulation that is compatible with the characterization methods. For example, characterization by a specific biochemical characterization method may require a solution state protein with targeted solution identity, while other characterization methods may rely on protein to be in dried form. Protein state, purity, concentration, solubility, and other features of the preparation may be assessed at this point. Gating metrics are typically protein purity, protein concentration, and (to the extent required) protein solubility. If the target formulation 408 is achieved, the protein sample is ready for characterization 409.

Protein Characterization

Protein preparations that are produced, purified, and modified as needed may then pass to the characterization phase 500. Protein characterization typically includes molecular, functional, and food science assays. Initially, all proteins may be evaluated in these assays to survey the candidate proteins to gain a range of output values. Each time through the discovery cycle, the number of characterized proteins increases, and it may be appropriate to reset the thresholds so that only highly promising proteins advance to the next step of characterization. Individual steps in this section generate data and metadata that is specific for each assay type for storing in the internal protein database.

Figure 7:
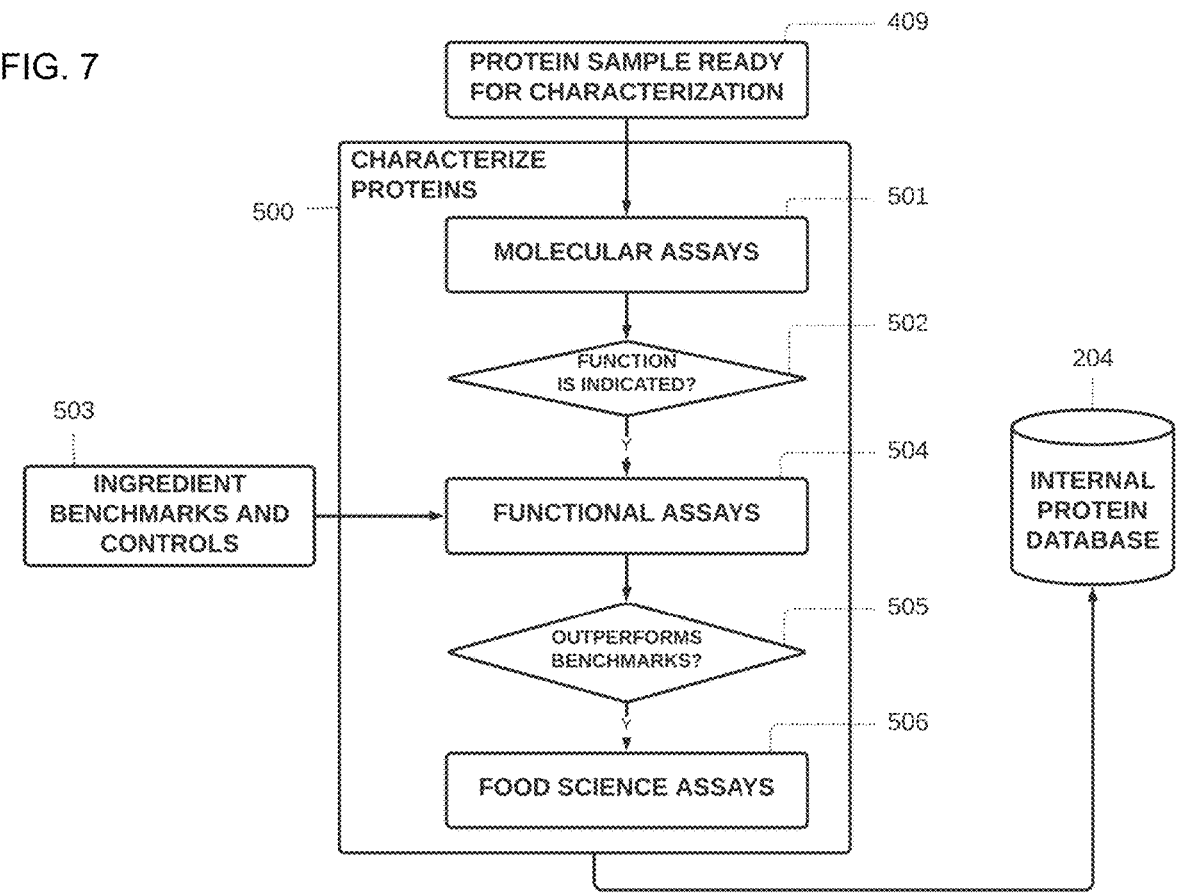
FIG. 7 shows the subsequent steps used to characterize candidate proteins by molecular assays 501, functional assays 504, and food science assays 506.

FIG. 7 illustrates the characterization phase. Molecular assays 501 that test physicochemical properties are used provide detailed biochemical and structural information for a protein of interest. Useful properties to test at this stage are illustrated in Table 2.

TABLE 2

Assessing biochemical properties

| Biochemical property | Assays |
|---|---|
| oligomerization state | size exclusion chromatography, native page |
| concentration | Bradford ™, Pierce 660 ™, absorbance spectroscopy |
| purity | amino acid analysis, proximate analysis, gel electrophoresis, capillary electrophoresis |
| buffering capacity | titration |
| pH | indicator strips, pH probe |
| enzyme activity | colorimetric assays, fluorometric assays, absorbance spectroscopy |
| molecular weight | gel electrophoresis, capillary electrophoresis |
| degradation | gel electrophoresis, amino acid analysis |
| conductivity | conductivity probe |
| % random coil | circular dichroism |
| % alpha helix | circular dichroism |
| % beta sheet | circular dichroism |
| zeta potential | phase analysis light scattering |
| solubility | fluorometric assays, colorimetric assays |
| aggregation | dynamic light scattering, centrifugation, size exclusion chromatography, fluorescence-based assays |
| particle size distribution | dynamic light scattering |
| melting temperature ($t_m$) | differential scanning calorimetry, thermal shift |

TABLE 2-continued

Assessing biochemical properties

| Biochemical property | Assays |
|---|---|
| heat capacity | assay differential scanning calorimetry, thermal shift assay |
| surface hydrophobicity | fluorometric assay |
| % thiols | fluorometric assay |
| sulfur content | fluorometric assay |
| density biophysical | |
| glycosylation content | mass-spectroscopy |

Data from the molecular assays 501 are usually stored in the internal database for use in retraining the predictive model, regardless of the result. Minimum criteria can be set to decide 502 which samples pass to functional assays 504. In the first rounds of the protein discovery, the user may decide to let all proteins pass through to functional assays, with the objective of building up the set of data used for training in the internal database 204. When predictive power of the models increases for a particular target function, the minimum criteria may be increased 502 to select only the most promising proteins to move to functional assays. Performance of the expressed proteins may also be compared with the performance of commercially available ingredient benchmarks 503, which are evaluated in functional assays 504 and in some cases food science assays 506. The benchmark ingredients may include animal-sourced ingredients as well as plant-based or synthetic ingredients that contain protein, starch, or lipid components.

Functional assays 504 performed on protein candidates include testing for the target function. Additional assays are typically included to characterize candidate proteins in other ways: such as for the presence of other desirable properties, the absence of undesirable properties, and other functions that may be collateral with the target function, and therefore relevant for the predictive modeling. Examples of such functional assays are listed in Table 3.

TABLE 3

Assessing functional properties

| Functional property | Assays |
|---|---|
| gelation | rheology |
| aggregation | dynamic light scattering |
| texture | texture profile analysis |
| particle size | dynamic light scattering |
| viscosity | viscometry |
| sol gel transition temperature | rheology |
| denaturation temperature | differential scanning calorimetry |
| heat capacity | differential scanning calorimetry |
| chewiness | texture profile analysis |
| color | colorimeter |
| storage modulus | rheology |
| shear strength | rheology |
| density | densitometry |
| swell ratio w/water | mass measurement |
| sedimentation layer thickness | emulsion stability analysis via multiple light scattering |
| sedimentation migration rate | emulsion stability analysis via multiple light scattering |
| emulsion stability index, coalescing phase | emulsion stability analysis via multiple light scattering |
| coalescence time | emulsion stability analysis via multiple light scattering |
| coalescing layer thickness | emulsion stability analysis via multiple light scattering |
| coalescence migration rate | emulsion stability analysis via multiple light scattering |

TABLE 3-continued

Assessing functional properties

| Functional property | Assays |
|---|---|
| emulsion stability index, flocculating phase | emulsion stability analysis via multiple light scattering |
| time to flocculation | emulsion stability analysis via multiple light scattering |
| flocculation layer thickness | emulsion stability analysis via multiple light scattering |
| flocculation migration rate | emulsion stability analysis via multiple light scattering |
| max foam volume | foam analysis via imaging |
| max liquid volume | foam analysis via imaging |
| gas volume foam | foam analysis via imaging |
| foam capacity | foam analysis via imaging |
| maximum foam density | foam analysis via imaging |
| foam expansion rate | foam analysis via imaging |
| foam half life time | foam analysis via imaging |
| drainage half life time | foam analysis via imaging |
| temperature at gelation point | rheology |
| yield stress | rheology |
| cohesiveness | texture profile analysis |
| adhesiveness | texture profile analysis |
| gumminess | texture profile analysis |
| melting point | differential scanning calorimetry |
| water binding capacity | moisture analysis |
| critical micelle concentration | dynamic light scattering |
| critical concentration for gelation | rheology |
| critical concentration for water binding | moisture analysis |
| antimicrobial action | microbial growth assays, fluorescent dye permeabilization, NMR spectroscopy |

The assays used in the characterization process may be standard or developed in-house. The project may include adapting assays to high-throughput formats or adapting typical food assays to probe a specific function of interest.

The properties of the target protein are measured and compared with benchmark samples selected to demonstrate the performance of the target protein with respect to commercially available ingredients. On this basis, a decision is made 505 as to which protein candidates proceed to food science assays 506. Promising candidates are tested in food model systems to validate the target protein's performance in a simplified food formulation. The performance information is stored in the internal protein database 204 and used to assess which proteins should be developed into products.

Figure 8:
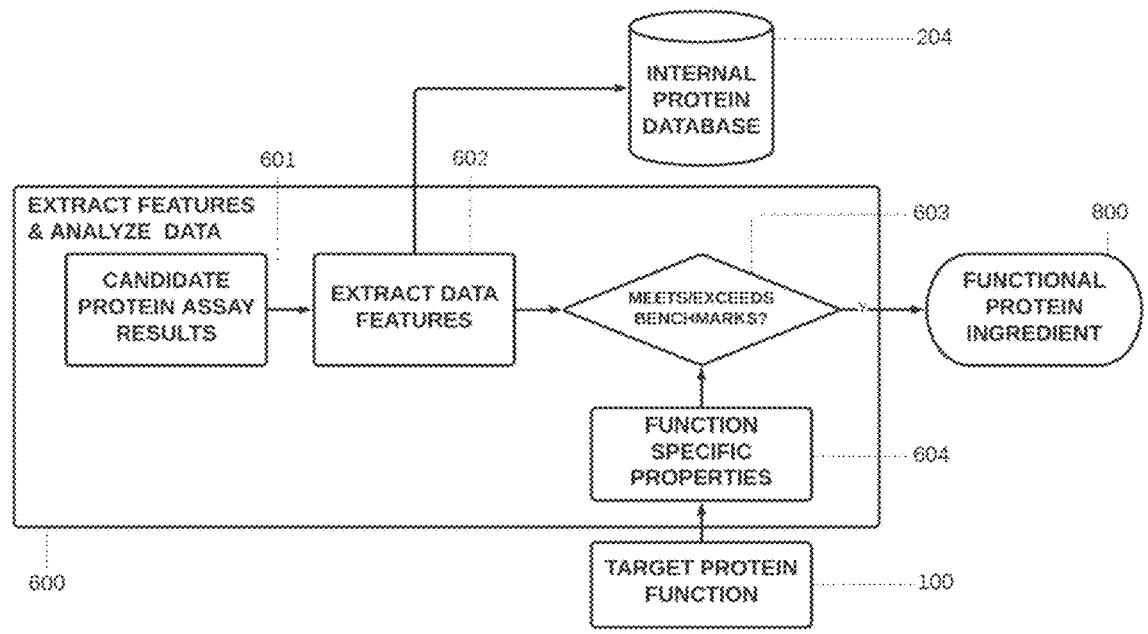
FIG. 8 shows details of how assay results 601 are extracted 602 for adding to the internal protein database 204 and used to evaluate 603 whether a protein candidate meet benchmarks, making it eligible for nomination as a potential food ingredient 800.

FIG. 8 provides a more detailed illustration of extracting features and analyzing the data 600. The raw data generated by characterization assays can vary widely by the assay type. Some common examples of data outputs include endpoint data, scalar values, sequences/series of scalar values (for example, time or temperature sequences), or images. The raw data are analyzed to extract meaningful trends.

Depending on the assay type, assay results for the protein candidates 601 can be tabular flat files, image files, or numerical values. The numerical values are interpreted as is. Tabular flat files and image files are processed to extract data features 602. The output may be a complete set of empirical data for the proteins that were characterized, which is used to evaluate whether the protein performed well and is entered into the protein database. The extraction process can comprise computing aggregated numerical values (such as mean or median of time series data) or extracting categorical values (such as color or transparency from images).

Each target protein function 100 is associated with a specific set of function specific properties 604 that can be used to determine whether a protein candidate is nominated as a potential food ingredient 800. The function specific properties 604 is a subset of biochemical and functional properties such as those listed in Table 2 and Table 3 that are related to target protein function and use of the candidate protein as a food ingredient. For example, if the target protein function 100 is foaming, then properties measured by the solubility, surface hydrophobicity, and foam analysis via imaging assays may be relevant for evaluation of the candidate proteins. Function specific properties 604 of a candidate protein are compared with benchmark thresholds 603 that are pre-established or developed during the course of discovery. The compared values are used to determine whether each protein candidate has sufficient target function 100 and other desirable properties at a level or combination that make it worthy to be nominated as a functional protein ingredient 800.

Active Learning

Figure 9:
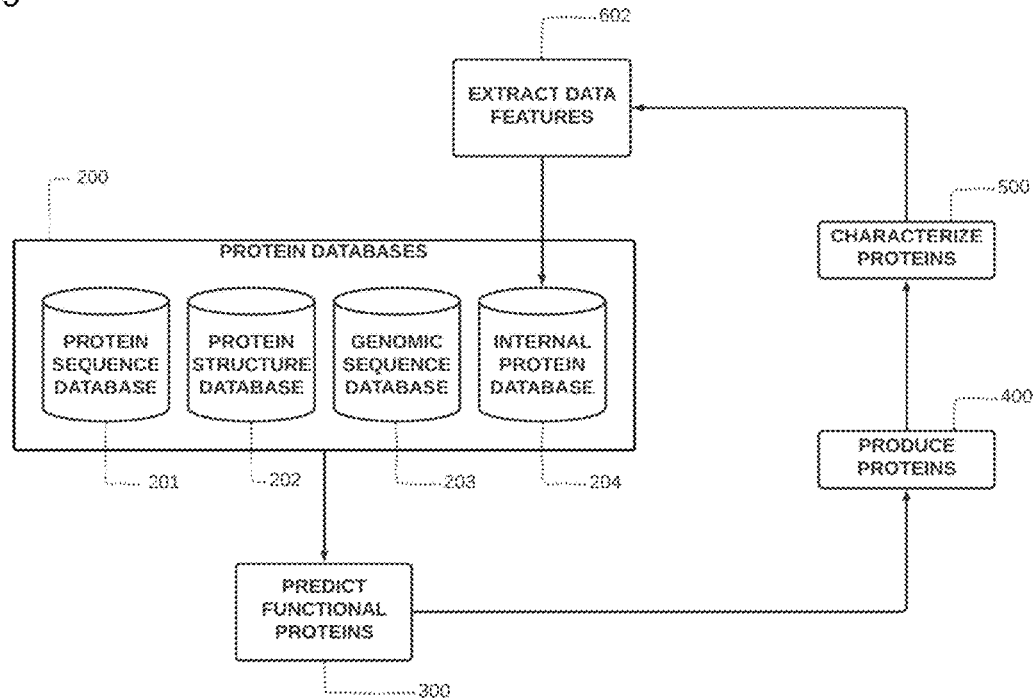
FIG. 9 shows how active learning extracts data from protein prediction 300, protein production 400 and characterization assays 500 and feeds it back into the internal database 204 to increase the power of the predictive modeling for the next iteration of the process.

FIG. 9 illustrates how technology in this disclosure may incorporate iterative active learning or retraining as part of the protein screening and characterization process. Information from the prediction and selection of protein candidates 300, protein production and purification 400, and the characterization of biochemical ad functional properties 500 provides useful data that can be extracted 602 and added to the internal protein database 204 for use in further training of the computer system.

If n is the number of iterative predictions run for a particular target function, then at n={0,1}, the internal protein database 204 will be empty. The ensemble methods will only be able to leverage protein data from the protein sequence, protein structure, and genomic sequence databases. For all n>1, additional information is available about selected and tested candidate proteins for the target function, which is added back into the internal protein database 294. The data for any iteration of n>1 will be used in the predictive modeling for iteration n+1. As the internal protein database will contain iteratively more information in n+1 than n, the predictive accuracy at n+1 will usually be higher than n.

Species Homologs and Isoforms

Proteins that play an important functional role in a botanical, zoological, or microbial context generally have homologs in closely related species of the source. A protein may also evolve within a species by gene duplication to create different isoforms. If a protein in a database scores high in the computer-driven predictive phase of this technology, there is an increased probability that species homologs and isoforms will also score high in the predictive phase.

It therefore can be beneficial to screen out homologs and isoforms during initial iterations of the discovery process so as to survey a broader range of unrelated structures. One homolog or isoform is selected for testing that represents the class. This can be done by temporarily removing homologs and isoforms from the list of candidates generated by the machine learning process, either by operator supervision or incorporation into the computer programming. Once a particular candidate is characterized empirically as having a high level of target function and other benefits, it may be appropriate to go back to the homologs and isoforms identified by the computer in the same class, producing and characterizing them separately so that the user can optimize the protein ultimately chosen as the food ingredient.

Screening for Additional Functional and Physicochemical Properties

The iterative discovery process of this disclosure optimally includes assessing whether the protein candidate has one or more additional desirable functions or properties, thereby increasing the favorability rating of the candidate—and assessing whether the protein candidate has one or more undesirable functions or properties, thereby decreasing the favorability rating of the candidate or removing it from contention. By way of illustration, desirable properties may include one or more of the following: ease of expression, ease of purification, stability on storage, mixability, and one or more desirable flavors or sensory properties. Undesirable properties may include one or more of the following: allergenicity or immunogenicity, incompatibility with other food ingredients, an adverse physiological effect, and an undesirable flavor.

Where computer prediction algorithms are available for such properties, the assessment may be done as part of the initial candidate selection process during protein screening and selection. The prediction algorithm for the respective property is used as part of scoring for each candidate, and optionally contributes to the machine learning function. For some categories such as toxicity, taste, and mouthfeel, assessment is done in the assay and empirical testing phases, or a combination of these with machine learning.

For example, allergenicity can be predicted in the manner of L. Zhang et al., Bioinformatics 2012, 28:2178-2179; L. Wang et al., Foods 2021, 10:809, doi.org/10.3390; and S. Saha et al., Nucl. Acids Res. 2006, 34, doi:10.1093. Immunogenicity can be predicted in terms of MHG binding motifs and T and B cell epitopes algorithmically in the manner of N. Doneva et al., Symmetry 2021:13, 388. Toxicity can be predicted in the manner of S. S. Negi et al., Sci. Reports 2017:7, 13957-1; and Y. Jin et al., Food Chem. Toxicol. 2017; 109:81-89. Aspects of flavor can be predicted in the manner of P. Keska et al., J. Sensory Studies 2017:e12301; F. Fritz et al., Nucleic Acids Res. 2021 Jul. 2; 49(W1): W679-W684' and S. Ployon et al., Food Chem. 2018 Jul. 1; 253:79-87.

Further Development and Approval of Functional Proteins as Food Ingredients

By putting this technology in place, the user can obtain a catalog of well categorized, functional protein ingredients with food-relevant functionalities. New ingredients identified by this technology may be produced for incorporation into commercial products by recombinant expression, either in the same form they occur in nature, or by producing only the parts of the protein that provide the target function. Knowledge of the ingredient source, method of scalable production, and a full panel of biochemical and functional characteristics that is generated as part of this discovery process is information that can be used to commercialize the newly discovered ingredients in a wide range of important applications.

After a new food ingredient has been identified according to this disclosure and formulated into a proposed new product, the developer will assure that all regulatory requirements are met before beginning commercial distribution. New food additives for distribution in the U.S. are subject to premarket approval by the Food and Drug Administration (FDA). The new addidtives are "generally recognized as safe" (GRAS) if there is generally available and accepted scientific data, information, or methods indicating it is safe, optionally corroborated by unpublished scientific data. A notification sent to FDA's Office of Food Additive Safety for approval includes a succinct description of the substance (chemical, toxicological and microbiolgcial characterization), the applicable conditions of use, and the basis for the GRAS determination. The FDA then evaluates whether the submitted notice provides a sufficient basis for a GRAS determination.

Other Implementations of the Discovery Process

Some implementations of the flywheel or discovery process put forth in this disclosure are a combination of the following methodologies:

Machine learning of how structural features of proteins (such as primary amino acid sequence, three-dimensional structure, vector representations, and known physicochemical properties) can be used to predict whether a previously uncharacterized protein has a target function;

Computer based mining of extensive sequence, structure, and functional databases to select protein candidates predicted to have the target function;

High-throughput expression and empirical testing of the candidates for the target function and other desirable characteristics;

Reiteration of the learning, database searching, expression, and testing to refine the selection process and select additional candidates.

In the preceding discussion, the discovery process has been illustrated by the selection and evaluation of potential new food ingredients to substitute for ingredients currently in widespread use and/or obtained from animal sources. The discovery process is equally suitable for identifying proteins that can substitute for or enhance functions in other industrial products and materials. Other possible applications of the discovery process include identifying proteins having the following potential uses in commerce:

ingredients for cosmetics structures for moisture retention binders for dyes optimized fermentation for manufacture of biofuels starting materials for polymer chemistry and plastics lubricants, surfactants, solubilizers, and dispersion enhancers coatings, ceramics, ink, and textiles agricultural feed having increased nutritional value encapsulation means, excipients and stabilizers for products in pharmaceutical industries.

Such alternative implementations of the discovery process represent alternative and included embodiments of the invention put forth in this disclosure. They may be claimed as additional or alternative aspects of this disclosure by adapting the claims presented below mutatis mutandis generically or in accordance with the selected or desired implementations.

Computer Hardware and Software

As a general matter, computer systems or microprocessors referred to in this disclosure are designed, manufactured, controlled, and programmed in accordance with standard methodology.

Figure 10:
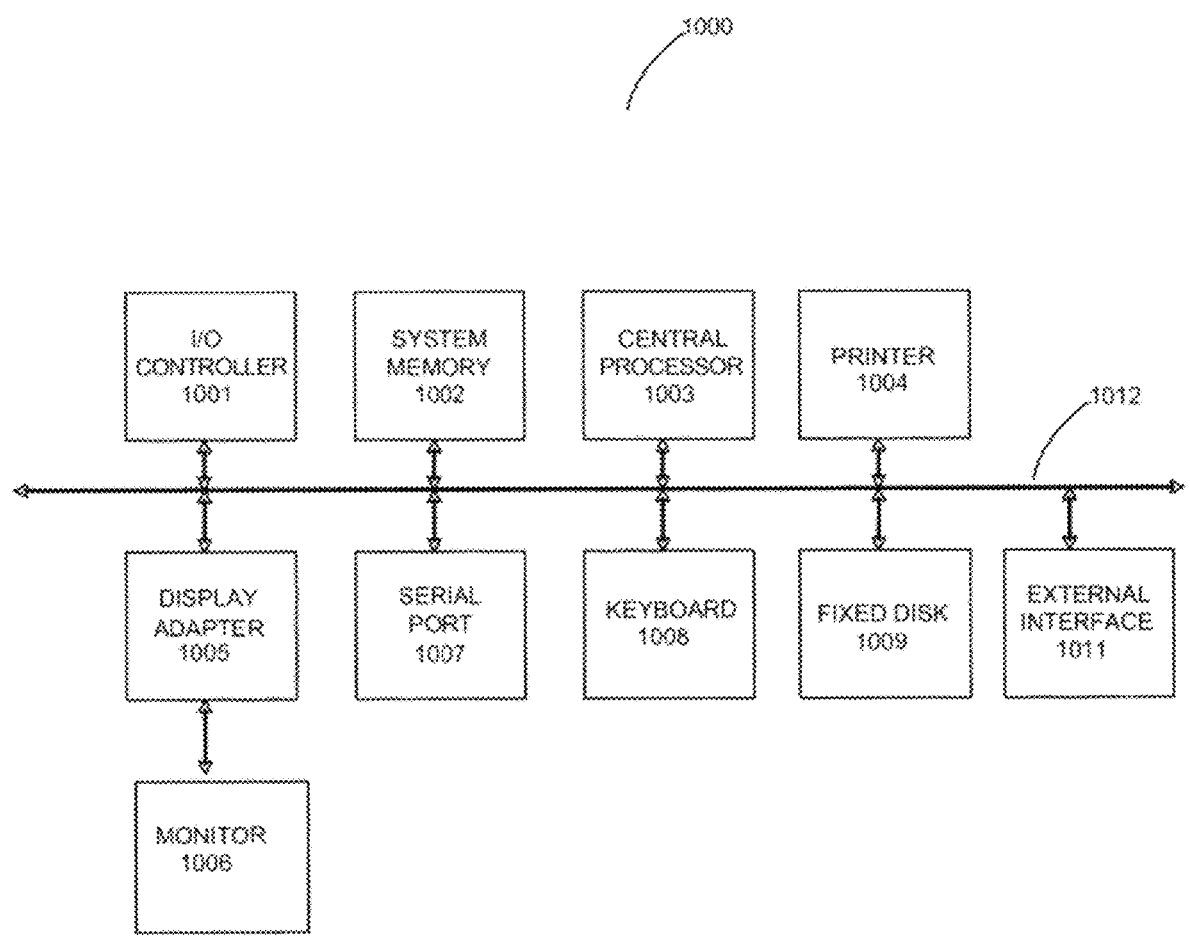
FIG. 10 shows subsystem architecture of a computer system by which protein selection, machine learning, and data calculation may be implemented in accordance with this disclosure.

FIG. 10 shows an arrangement for a computer system that is either a single apparatus or assembly, or an interconnected plurality thereof. Subsystems of the computer system are typically interconnected via a system bus 1012. Subsystems may include a printer 1004, keyboard 1008, fixed disk 1009, and monitor 1006, which may be operably connected to a display adapter 1005. Peripherals and input/output devices coupled to an I/O controller 1001 may be operably connected to the computer system by a suitable means such as a USB port 1007 and/or an external interface 1011, which may also connect the computer system to wide area network such as the Internet. Interconnection of subsystems via the system bus 1012 allows the central processor or microprocessor 1003 to communicate with each subsystem and control the execution of instructions from system memory 1002 or other memory means such as a fixed disk 1009, as well as the exchange of information between subsystems.

External databases containing useful information, such as information on protein sequence, structure, and characteristics, may be sourced through a public network such as the Internet. Internal databases of information may be part of the computer system or sourced through a secure network. When information is sourced in the course of calculating, evaluating, or machine learning in accordance with this disclosure, the information may come from one or a combination of different databases that are external and/or internal. The computer system may transfer information or calculations from one component to another component or output information to a user, who can input information or direction back into the computer system and thereby to its components.

Operations or functions referred to in this disclosure may be implemented as software code to be executed by a processor. Machine learning languages include Python, Pytorch, Scala, Java, R Programming, Javascript, Lisp, SageMaker, and C++. Reference books on the subject include *Data-Driven Science and Engineering*, S. L. Brunton, 2019; *Machine Learning for* [patent attorneys and other] *Dummies*, J. P. Meuller, 2nd Ed, 2021; and *Deep Learning*, I. Goodfellow et al., 2016.

The software code may be stored as a series of instructions or commands on a computer readable medium for storage and/or transmission, such as random access memory (RAM), a read only memory (ROM), a magnetic medium such as a hard-drive, an optical medium such as a DVD (digital versatile disk), flash memory, or in information packets downloadable from a vendor or source via an electronic network. Any of the methods referred to in this disclosure may be totally or partially performed with a computer system configured or programmed to perform the steps of the method, in combination with or independent from input or supervision from a user. Method steps referred to in this disclosure that are performed entirely or in part by a computer system are optional unless otherwise stated or required.

INCORPORATION BY REFERENCE

Each and every publication and patent document cited in this disclosure is hereby incorporated herein by reference in its entirety for all purposes to the same extent as if each such publication or document was specifically and individually indicated to be incorporated herein by reference.

INTERPRETATION AND IMPLEMENTATION

Although the technology described above is illustrated in part by certain concepts, procedures, and information, the claimed invention is not limited thereby except with respect to the features that are explicitly referred to or otherwise required. Theories that are put forth in this disclosure with respect to the underlying mode of production, action, and assessment of various products and components are provided for the interest and possible edification of the reader, and do not limit practice of the claimed invention. The reader may use the technology put forth in this disclosure for any suitable purpose.

While the invention has been described with reference to the specific examples and illustrations, changes can be made and substituted to adapt to a particular context or intended use as a matter of routine development and optimization and within the purview of one of ordinary skill in the art, thereby achieving benefits of the invention without departing from the scope of what is claimed below and equivalents thereof

The invention claimed is:

1. A method of identifying and developing individual naturally occurring proteins as food ingredients, the method comprising:
   (a) training a computer system to predict whether an individual protein has a preselected target food function from structural characteristics and properties of the protein,
   wherein the target food function is a desired effect of the individual protein on a commercial food product when incorporated into the food product as an ingredient,
   wherein the structural characteristics and properties of the protein used to train the computer system include at least the protein's amino acid sequence,
   wherein the computer system is trained by a process of machine learning that comprises inputting into the computer system a training data set that contains said characteristics and properties for a plurality of individual proteins known to have the target food function and for a plurality of individual proteins known not to have the target food function;
   (b) applying the computer system trained in step (a) to a database that contains said characteristics and properties for each of a plurality of naturally occurring individual proteins for which it is not previously known whether the individual proteins have the target food function, thereby predicting which of the naturally occurring individual proteins in the database have the target food function;
   (c) identifying or ranking by the computer system the naturally occurring individual proteins predicted in step (b) to have the target food function, thereby obtaining a set of protein candidates;
   (d) recombinantly expressing and purifying each of the protein candidates;
   (e) conducting assays to determine or quantify which of the expressed protein candidates have the target food function;
   (f) adding structural data and/or assay results for the protein candidates tested in step (e) into the training data set;
   (g) selecting one or more of the individual proteins assayed in step (e) as potential food ingredients if they are determined in step (e) as having the target food function above a chosen threshold;
   (h) performing additional cycle(s) of steps (a) to (g) until a desired number of individual proteins have been selected as potential food ingredients having the target food function above the threshold; and then
   (i) assessing one or more individual proteins selected as potential food ingredients in step (h) to determine whether it meets desired performance requirements as part of a food preparation.

2. The method of claim 1, wherein the target food function is selected from antimicrobial activity, gelation, moisture retention, fat structuring, adhesion, fiber formation, and particular flavors.

3. The method of claim 2, wherein the target food function is gelation, wherein the individual protein binds other ingredients at low concentrations and forms a gel when heated.

4. The method of claim 2, wherein the target food function is a particular flavor.

5. The method of claim 3, wherein one or more of the individual proteins selected as potential food ingredients in step (h) are assessed in step (i) as an egg replacement in a food preparation.

6. The method of claim 1, wherein the machine learning includes deep learning and homology comparison of the individual proteins.

7. The method of claim 1, wherein the characteristics analyzed in the training in step (a) and the applying in step (b) includes a homology comparison of amino acid sequences of the individual proteins.

8. The method of claim 1, wherein the structural characteristics analyzed in the training in step (a) and the applying in step (b) further include a homology comparison of three-dimensional structure of each individual protein, obtained from crystallography data or predicted from the protein's amino acid sequence.

9. The method of claim 1, wherein the properties analyzed in the training in step (a) and the applying in step (b) further include a homology comparison of vector representations of physicochemical and biochemical properties of amino acids and clusters of amino acids of each individual protein.

10. The method of claim 1, wherein the identifying of protein candidates in step (c) and/or the selecting of potential food ingredients in step (g) also includes assessing whether the protein candidate or potential food ingredient has or is predicted to have one or more additional desirable functions or properties.

11. The method of claim 10, wherein the other desirable functions or properties include one or more of the following: ease of expression, ease of purification, stability on storage, mixability, and one or more desirable flavors or sensory properties.

12. The method of claim 1, wherein the identifying of protein candidates in step (c) and/or the selecting of potential food ingredients in step (g) also includes removing a protein as a protein candidate or potential food ingredient if it has or is predicted to have one or more undesirable functions or properties.

13. The method of claim 12, wherein the undesirable functions or properties include one or more of the following: predicted allergenicity or immunogenicity, incompatibility with other food ingredients, an adverse physiological effect, and an undesirable flavor.

14. The method of claim 1, further comprising selecting and removing one or more individual proteins identified as species homologs and/or isoforms from the set of protein candidates before step (d).

15. The method of claim 1, wherein step (d) is a high throughput expression and purification process wherein each of a plurality of protein candidates identified in step (c) are expressed as a fusion protein also containing an amino acid tag sequence, and the protein candidates are purified by affinity separation using a conjugate binding partner for the tag sequence before the assays are conducted in step (e).

16. The method of claim 15, wherein the tag is left on protein candidates for conducting at least some of the assays of step (e), but removed from potential food ingredients for assessing whether they meet the desired performance requirements in step (i).

17. The method of claim 1, wherein the expressing and purifying in step (d) and the assaying in step (e) are repeated one or more times to improve volume and/or quality of protein production.

18. The method of claim 1, wherein the assaying in step (e) includes determining or measuring one or more physicochemical properties of the protein candidates selected from thermal stability, buffering capacity, solubility, and charge.

19. The method of claim 1, wherein the assaying in step (e) includes determining or measuring one or more functional properties of the protein candidates selected from emulsion stability, foam stability, gelation, chewiness, storage modulus, water binding capacity, swell ratio in water, sedimentation rate, adhesiveness, antimicrobial activity, and enzyme activity.

20. The method of claim 1, further comprising unmasking and testing an individual protein that was predicted by the computer system in step (c) as having the target food function but was determined not to have the target food function when assayed in step (e), the unmasking comprising:

recombinantly expressing and purifying a potentially unmasked version of the individual protein in which a part of the protein predicted to have the target food function is excised from other parts of the protein that are believed to mask the target food function, and then conducting additional assays to determine or measure whether the potentially unmasked version of the protein has the target food function.

21. The method of claim 1, wherein the performance requirements tested in step (i) include demonstration of the target food function by the potential food ingredient when compounded into a food product, and compliance of the food product with regulatory requirements.

22. The method of claim 1, further comprising:

(j) manufacturing a food product in which a conventional food ingredient having said target food function is replaced with one or more individual proteins assessed in step (i) as meeting the desired performance requirements.

23. The method of claim 22, wherein the food product is a vegan equivalent of a sausage or a meat patty.

24. The method of claim 22, wherein the food product is a baked good or a confectionary.

* * * * *